US008675196B2

(12) United States Patent
Ozasa (10) Patent No.: US 8,675,196 B2
(45) Date of Patent: Mar. 18, 2014

(54) ANALYZER AND PARTICLE IMAGING METHOD

(75) Inventor: Masatsugu Ozasa, Kobe (JP)

(73) Assignee: Sysmex Corporation, Kobe (JP)

( * ) Notice: Subject to any disclaimer, the term of this patent is extended or adjusted under 35 U.S.C. 154(b) by 423 days.

(21) Appl. No.: 12/914,269

(22) Filed: Oct. 28, 2010

(65) Prior Publication Data

US 2011/0102792 A1 May 5, 2011

(30) Foreign Application Priority Data

Oct. 30, 2009 (JP) ................................ 2009-251377

(51) Int. Cl.
*G01N 21/00* (2006.01)
*G01J 1/10* (2006.01)

(52) U.S. Cl.
USPC ......... 356/337; 356/340; 356/432; 356/243.2

(58) Field of Classification Search
USPC ................................................ 356/335–344
See application file for complete search history.

(56) References Cited

U.S. PATENT DOCUMENTS

| | | | | |
|---|---|---|---|---|
| 3,940,608 | A * | 2/1976 | Kissinger et al. | 250/227.28 |
| 4,786,165 | A | 11/1988 | Yamamoto et al. | |
| 5,416,580 | A * | 5/1995 | Trainer | 356/336 |
| 5,824,269 | A * | 10/1998 | Kosaka et al. | 422/73 |
| 6,190,877 | B1 * | 2/2001 | Adair | 435/29 |
| 6,248,590 | B1 * | 6/2001 | Malachowski | 436/63 |
| 6,354,724 | B1 * | 3/2002 | Sakashita | 362/558 |
| 6,411,420 | B1 | 6/2002 | Yamada et al. | |
| 6,519,033 | B1 * | 2/2003 | Quist et al. | 356/337 |
| 7,130,672 | B2 * | 10/2006 | Pewzner et al. | 600/324 |
| 7,603,166 | B2 * | 10/2009 | Casscells et al. | 600/473 |
| 7,990,525 | B2 * | 8/2011 | Kanda | 356/73 |
| 7,999,937 | B1 * | 8/2011 | Srivastava et al. | 356/338 |
| 2002/0141625 | A1 * | 10/2002 | Nelson | 382/131 |
| 2003/0091277 | A1 * | 5/2003 | Mei | 385/33 |
| 2004/0061853 | A1 * | 4/2004 | Blasenheim | 356/318 |
| 2008/0108103 | A1 | 5/2008 | Ishisaka et al. | |
| 2008/0221711 | A1 * | 9/2008 | Trainer | 700/54 |
| 2010/0196917 | A1 * | 8/2010 | Ishisaka et al. | 435/6 |

FOREIGN PATENT DOCUMENTS

| | | |
|---|---|---|
| CN | 1802184 A | 7/2006 |
| CN | 101326428 A | 12/2008 |
| JP | 06-167640 A | 6/1994 |
| JP | 09-311103 A | 12/1997 |
| JP | 10-073528 A | 3/1998 |
| JP | 2001-074643 A | 3/2001 |
| JP | 2003-156698 A | 5/2003 |
| WO | WO 99/49354 A1 | 9/1999 |
| WO | WO 2004/083817 A2 | 9/2004 |
| WO | WO 2006/103920 A1 | 10/2006 |
| WO | WO 2007/044821 A | 4/2007 |
| WO | WO 2009/057525 A1 | 5/2009 |

OTHER PUBLICATIONS

Byun, Insoo et al., "A micro flow cell cytometry based on MEMS technologies using silicon and optical fibers," Journal of Materials Science, vol. 38, 2003, pp. 4603-4605.

\* cited by examiner

*Primary Examiner* — Michael A Lyons
*Assistant Examiner* — Jarreas C Underwood
(74) *Attorney, Agent, or Firm* — Brinks Gilson & Lione (57) ABSTRACT

An analyzer comprises: a sample stream forming section for forming a sample stream including particles; a light source; an optical fiber bundle formed by a plurality of optical fibers, into which light from the light source enters, and which emits light onto the sample stream; and an imaging device for imaging a particle in the irradiated sample stream.

20 Claims, 10 Drawing Sheets

Fig. 10

ANALYZER AND PARTICLE IMAGING METHOD

RELATED APPLICATIONS

This application claims priority under 35 U.S.C. §119 to Japanese Patent Application No. 2009-251377 filed on Oct. 30, 2009, the entire content of which is hereby incorporated by reference.

FIELD OF THE INVENTION

The present invention relates to an analyzer with a function for imaging particles in a sample stream irradiated by light, and a particle imaging method for same.

BACKGROUND OF THE INVENTION

Japanese Patent Publication No. 2001-74643 discloses a particle analyzer which includes a sheath flow cell for forming a sample stream by a sheath fluid and a sample containing particles such as cells or the like, a pulse light source for emitting a light pulse, optical fiber for guiding the light pulse emitted from the pulse light source, condenser lens for collecting the light pulse emitted from the pulse light source and irradiating the sample stream, and a video camera for capturing a projection image of the particles in the sample stream irradiated by the light pulse.

In this particle analyzer, coherency can be reduced to obtain particle images of small refraction fringes (interference fringes) by passing the light pulse emitted from the pulse light source through the optical fiber.

Figure 9:
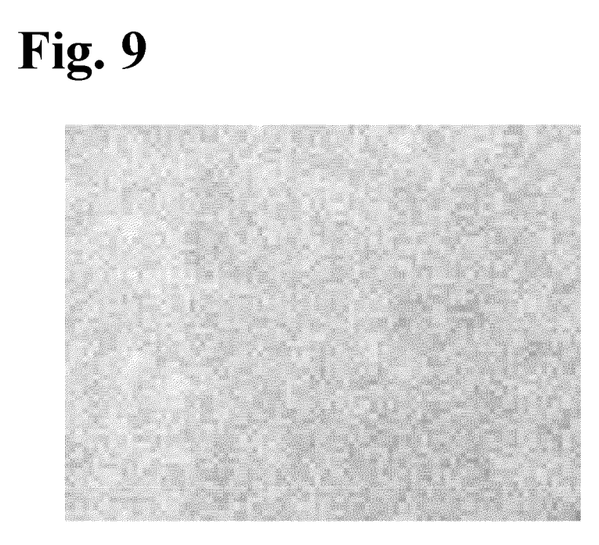
FIG. 9 is a background image captured by the imaging section of the conventional art.

However, when imaging a particle irradiated by the light pulse that has passed through the optical fiber, speckle noise (black and white spotted background) such as shown in FIG. 9 may appear in the image. Speckle noise is caused by random interference between modes within the optical fiber, defects inside the optical fiber and distortion of the core diameter, and expansion of the core diameter due to temperature fluctuation.

SUMMARY OF THE INVENTION

The scope of the present invention is defined solely by the appended claims, and is not affected to any degree by the statements within this summary.

A first aspect of the present invention is an analyzer, comprising: a sample stream forming section for forming a sample stream including particles; a light source; an optical fiber bundle formed by a plurality of optical fibers, into which light from the light source enters, and which emits light onto the sample stream; and an imaging device for imaging a particle in the irradiated sample stream.

A second aspect of the present invention is a particle imaging method, comprising steps of: forming a sample stream including particles; guiding light from a light source into an optical fiber bundle formed by a plurality of optical fibers; emitting the light, that has entered the optical fiber bundle from the light source, from the optical fiber bundle to irradiate the sample stream; and imaging the particles in the irradiated sample stream.

BRIEF DESCRIPTION OF THE DRAWINGS

FIG. 7($a$) is a view on the A-A line of FIG. 6, and FIG. 7($b$) is a view on the B-B line of FIG. 6.

DETAILED DESCRIPTION OF THE EMBODIMENT

The embodiment of the cell analyzer and cell analysis method of the present invention is described in detail hereinafter with reference to the accompanying drawings.
[General Structure of the Cell Analyzer]

Figure 1:
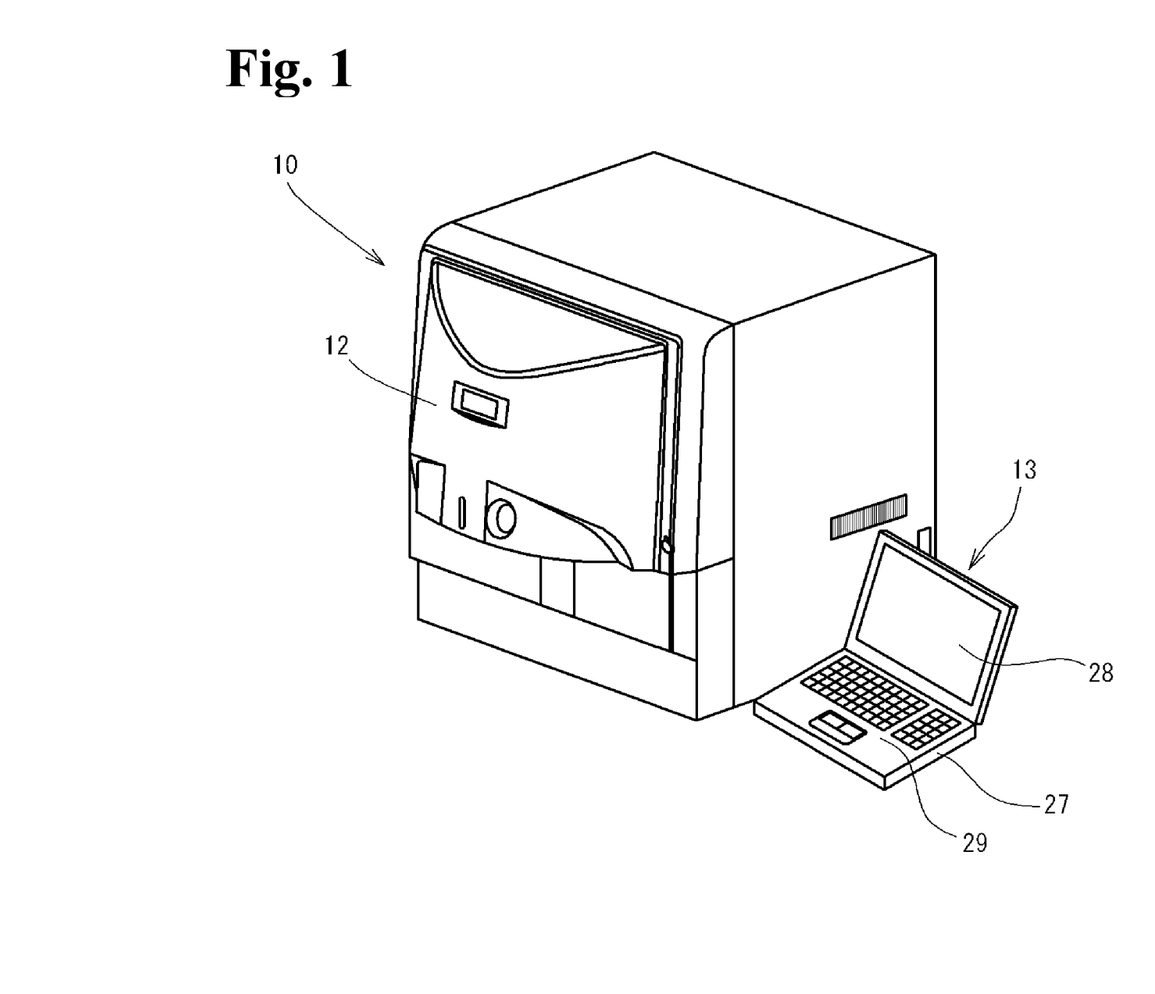
FIG. 1 is a perspective diagram of a cell analyzer of an embodiment of the present invention.

FIG. 1 is a perspective diagram of a cell analyzer 10 of the embodiment of the present invention. The cell analyzer 10 determines whether cancer cells and idioblasts (hereinafter referred to as abnormal cells) are contained among the cells and captures images of the light-irradiated cells by flowing a measurement sample containing cells (particles) collected from a patient through a flow cell, irradiating the sample stream flowing through the flow cell, and detecting and analyzing the light (forward scattered light, side fluorescent light and the like) from the cells in the measurement sample. Specifically, the cell analyzer 10 of the present embodiment is used to screen epithelial cells collected from the cervix to detect cervical cancer cells.

The cell analyzer 10 is provided with a main body 12 for performing sample measurements and the like, and a system controller 13, which is connected to the main body 12, and performs analysis of the measurement results.

Figure 2:
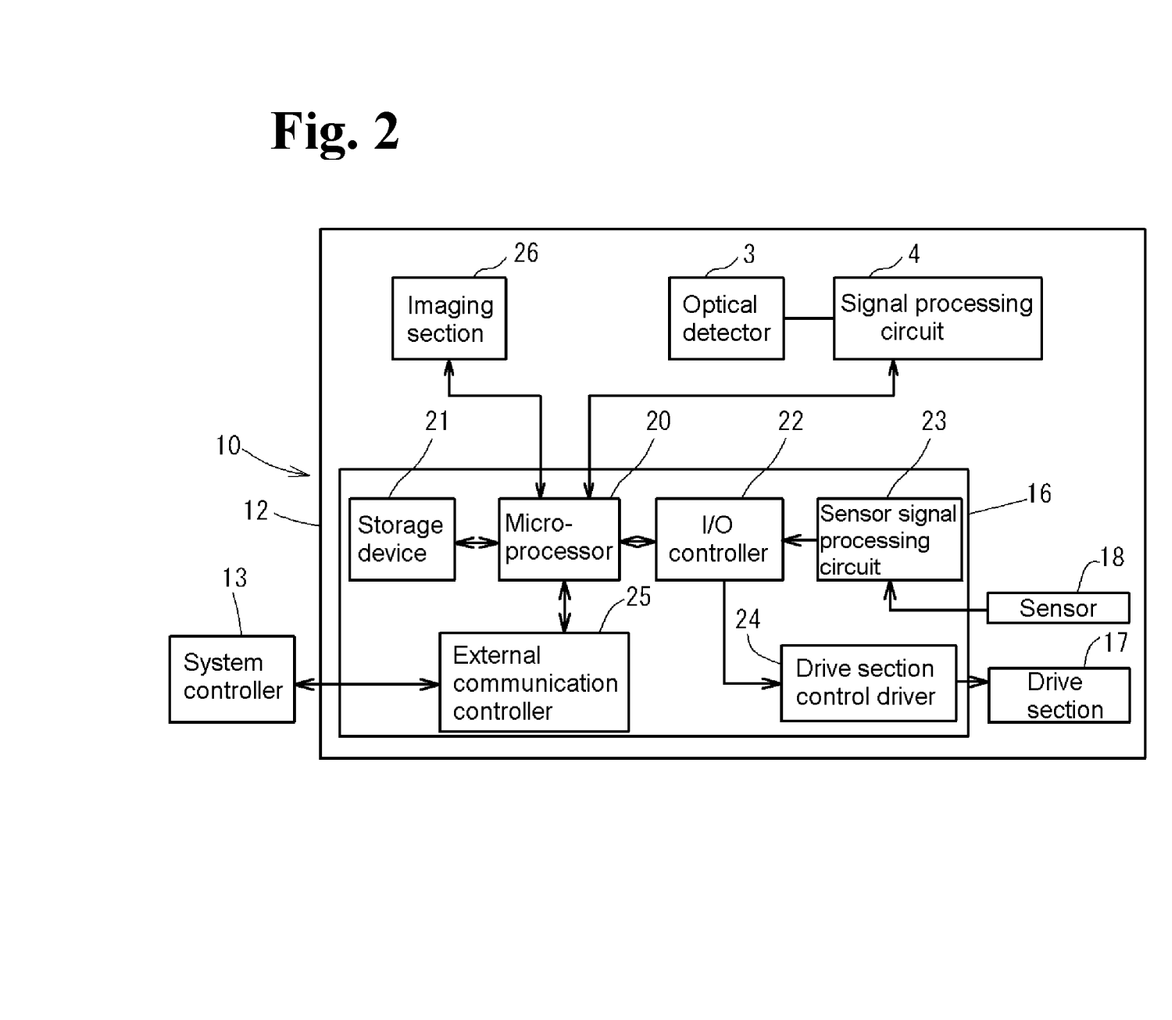
FIG. 2 is a block diagram showing the structure of the cell analyzer of FIG. 1.

As shown in FIG. 2, the main body 12 of the cell analyzer 10 is configured by an optical detector 3 for detecting information such as the cells and size of nuclei from the measurement sample, signal processing circuit 4, measurement controller 16, a drive section 17 including a motor, actuator, valve and the like, various sensors 18, and imaging section 26 for capturing an image of a cell.

The signal processing circuit 4 has an analog signal processor for amplifying the output of the optical detector 3 and performing amplification processing and filter processing of the amplified signals, an A/D converter for converting the output of the analog signal processor to digital data, and digital signal processor for performing waveform processing of the digital data.

The measurement controller 16 also aspirates and measures the measurement sample by controlling operation of the drive section 17 while processing the signals of the sensors 18. When screening for cervical cancer, the measurement sample may be prepared using well known processes such as PI staining, agitation (tapping), dilution (wash) centrifuge (concentration) of cells (epithelial cells) collected from the cervix of the patient. The prepared measurement sample is accommodated in a test tube positioned below a pipette (not shown in the drawing) of the main body 12, aspirated together with sheath fluid via the pipette, and supplied to the flow cell to form a sample stream in the flow cell. The PI staining is performed using propidium iodide, a fluorescent stain that contains a dye. In PI staining, fluorescent light from the nucleus can be detected by selective staining the nucleus.

[Structure of the Measurement Controller]

The measurement controller 16 is provided with a microprocessor 20, storage part 21, I/O controller 22, sensor signal processor 23, drive control driver 24, and external communication controller 25 and the like. the storage part 21 is configured by a ROM, RAM and the like; the ROM stores the control program for controlling the drive section 17 and the data required to execute the control program. The microprocessor 20 loads the control program into the RAM, or directly executes the control program from the ROM.

Signals from the sensors 18 are transmitted through the sensor signal processor 23 and I/O controller 22 to the microprocessor 20. The microprocessor 20 controls the drive section 17 through the I/O controller 22 and drive control driver 24 according to the signals from the sensors 18 by executing the control program.

The data processed by the microprocessor 20 and the data required for processing by the microprocessor 20 are transmitted and received between the microprocessor 20 and external devices such as the system controller 13 via the external communication controller 25.

[Structure of the System Controller]

As shown in FIG. 1, the system controller 13 is a personal computer or the like mainly configured by a body unit 27, display unit 28, and input unit 29. The body unit 27 is provided with a CPU, ROM, RAM, hard disk, reading device, I/O interface, image output interface and the like.

An operating system such as Windows (registered trademark), application programs, and the data used to execute the programs are installed on the hard disk; and these programs are executed by the CPU. The application programs include programs for transmitting measurement orders (operation instructions) to the measurement controller 16, receiving and processing the measurement results obtained by the main body 12, and displaying the processed analysis results.

The I/O interface of the system controller 13 is connected to the main body 12, to enable sending and receiving of data between the system controller 13 and the main body 12. The image output interface of the system controller 13 is connected to the display unit 28, such as an LCD or CRT; the image signals corresponding to the image data received from the CPU are output to the display unit 28.

[Structures of the Optical Detection Section and Imaging Section]

Figure 3:
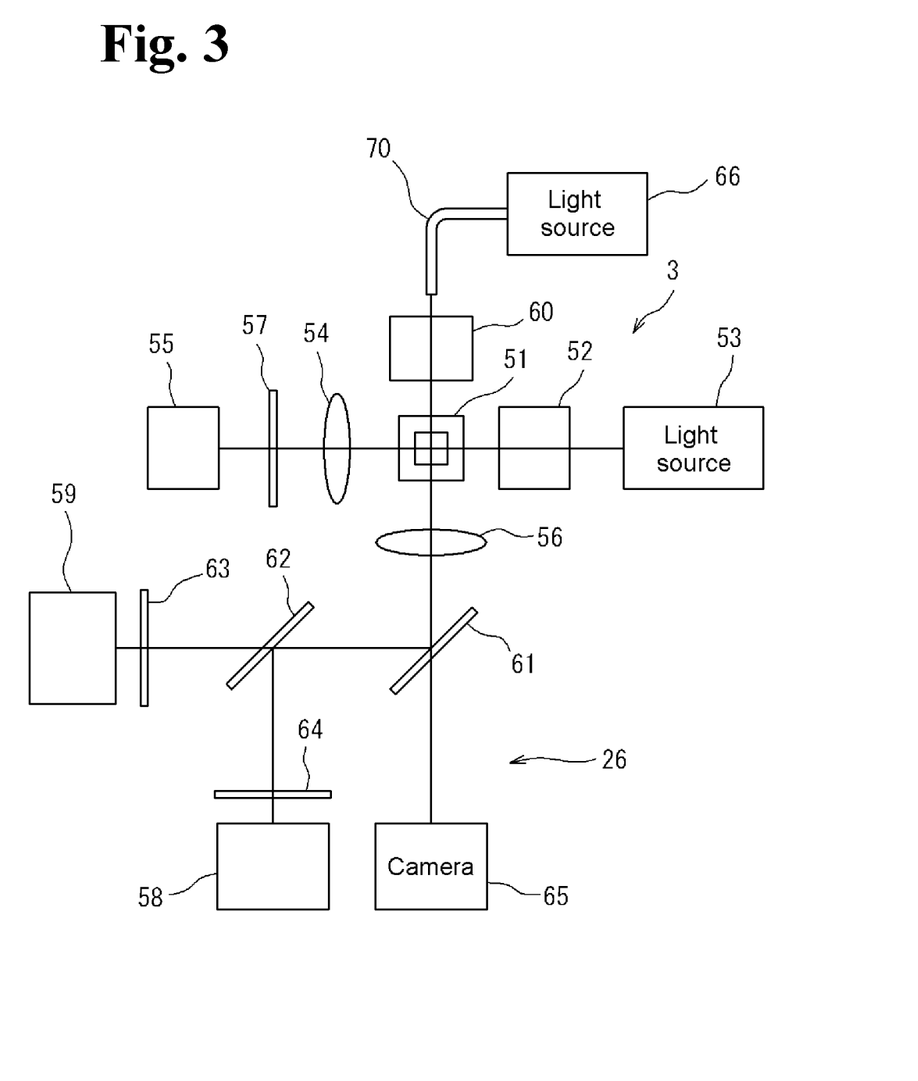
FIG. 3 shows the structure of the optical detection section.

FIG. 3 shows the structures of the optical detection section 3 and the imaging section 26. The optical detector 3 is provided with a semiconductor laser light source 53; the laser light emitted from the light source 53 passes through the lens system 52 and focused on the measurement sample (sample stream) flowing through the flow cell 51. The forward scattered light from the cells in the measurement sample irradiated by the laser light passes through an objective lens 54 and filter 56, and is detected by a photodiode (first detector) 55. Note that the lens system 52 is configured by a lens group that includes a collimator lens, cylindrical lens, condenser lens and the like.

The side fluorescent light and side scattered light from the cell passes through an objective lens 56 disposed at the side of the flow cell 51, and enters a dichroic mirror 61. The side fluorescent light and side scattered light reflected by the dichroic mirror 61 enters a dichroic mirror 62, and the side fluorescent light that passes through the dichroic mirror 62 also passes through a filter 63 and is detected by a photomultiplier (second detector) 59. The side scattered light reflected by the dichroic mirror 62 passes through a filter 64, and is detected by a photomultiplier (third detector) 58.

The photodiode 55, photomultiplier 58, and photomultiplier 59 convert the detected light to electrical signals, and respectively output a forward scattered light signal (FSC), side scattered light signal (SSC), and side fluorescent light signal (SFL). These signals are amplified by amplifiers not shown in the drawing, and thereafter the amplified signals are transmitted to the previously mentioned signal processing circuit 4 (refer to FIG. 2).

As shown in FIG. 2, the signal processing circuit 4 performs signal processing such as filter processing, A/D conversion processing and the like on signals to obtain the forward scattered light data (FSC), side scattered light data (SSC), and side fluorescent light data (SFL). The measurement controller 16 uses the aforesaid data to obtain various characteristic parameters. The characteristic parameters are, for example, the signal waveform pulse width (FSCW) of the forward scattered light, signal waveform peak value (FSCP) of the forward scattered light, peak value (PEAK) of the fluorescent light signal waveform, integral difference (DIV) of the fluorescent light signal waveform, pulse width (SSCW) of the side scattered light signal waveform, and area (fluorescence amount) (SFLI) of the fluorescent light signal pulse.

The measurement data (light data and characteristic parameters) are transmitted by the microprocessor 20 through the external communication controller 25 to the previously mentioned system controller 13, where the data are stored on the hard disk. The system controller 13 discriminates whether the cell is abnormal based on the forward scattered light data (FSC), side scattered light data (SSC), side fluorescent light data (SFL), and characteristic parameters. The CPU of the system controller 13 performs predetermined analyses based on the abnormal cell discrimination result, for example, calculating the ratio of abnormal cells.

The ratio of abnormal cells is the percentage of abnormal cells among the cells of the object of analysis, and describes the relationship between the number of abnormal cells X and the number of normal cells Z and can be expressed, for example, by equation (1) below.

$$\text{Ratio of abnormal cells: } W = X/(X+Z) \tag{1}$$

The ratio of abnormal cells is displayed on the display unit 28 of the system controller 13 as an analysis result, and is useful in the diagnosis by physicians and cell pathologists. The CPU of the system controller 13 creates a FSCW-FSCP scattergram with the pulse width (FSCW) plotted on the horizontal axis and the peak value (FSCP) plotted on the vertical axis, and creates a (DIV-PEAK)-SSCW scattergram of the signal waveform pulse width (SSCW) of the side scattered light signal waveform plotted on the horizontal axis using the value of (DIV-PEAK) obtained by dividing the integral difference (DIV) of the fluorescent light signal waveform by the peak value (PEAK) plotted on the vertical axis.

The main body 12 of the present embodiment is provided with an imaging section 26 in addition to the optical detector 3. The imaging section 26 is provided with a pulse laser light source 66 and CCD camera (imaging device) 65; The pulse laser light from the light source 66 passes through optical fiber bundle 70 and lens system 60 and enters the flow cell 51, then passes through the objective lens 56 and dichroic mirror 61 to ultimately form and image in the CCD camera 65.

The light source 66 emits light with a timing for imaging, via the camera 65, the abnormal cell discriminated in the system controller 13. The light source 66 of the present embodiment emits a pulse of laser light having coherence of 150 μm, with an emission time of less than 10 nsec (for example, approximately 6.8 nsec) to image, without blurring, particles flowing in the flow cell 51 at a flow speed of approximately 13.3 m/sec.

As shown in FIG. 2, the image of the abnormal cell captured by the camera 65 is transmitted by the microprocessor 20 to the system controller 13 via the external communication controller 25. The image of the abnormal cell is then associated with the characteristic parameters determined based on the forward scattered light data (FSC), side scattered light data (SSC), side fluorescent light data (SFL) of the cell.

[Structures of the Lens System and Optical Fiber Bundle]

Figure 4:
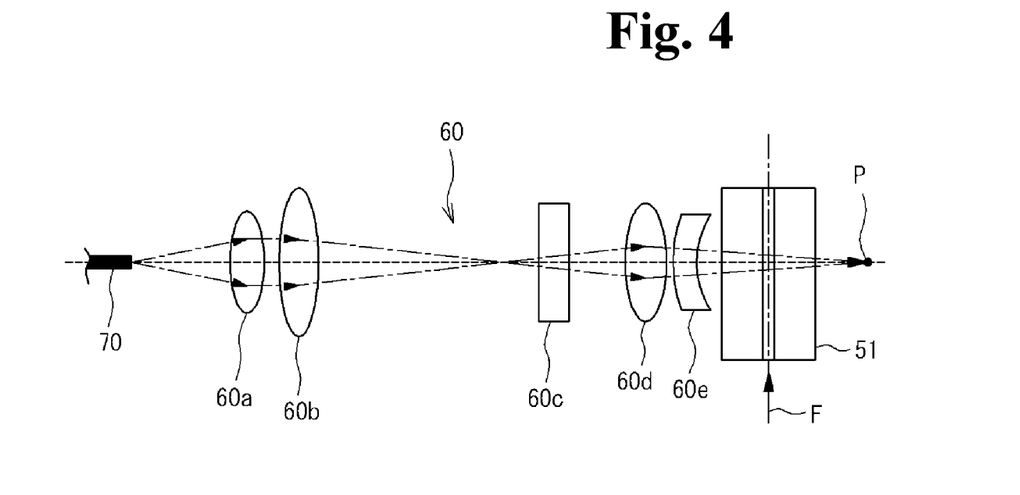
FIG. 4 is a side view of the lens system.
Figure 5:
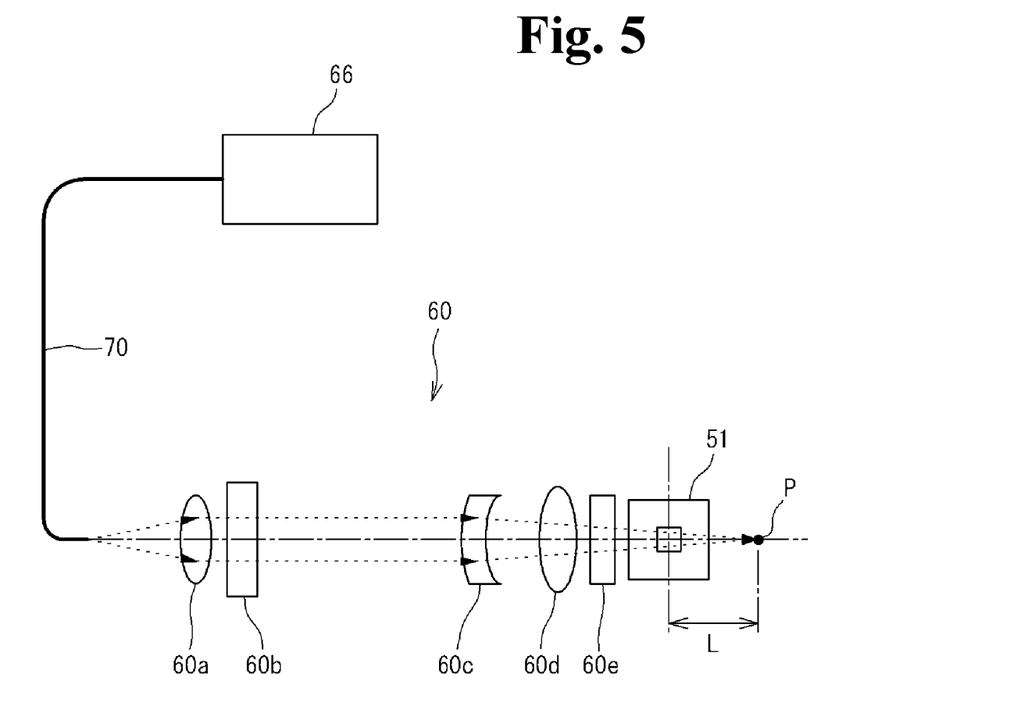
FIG. 5 is a top view of the lens system.
Figure 6:
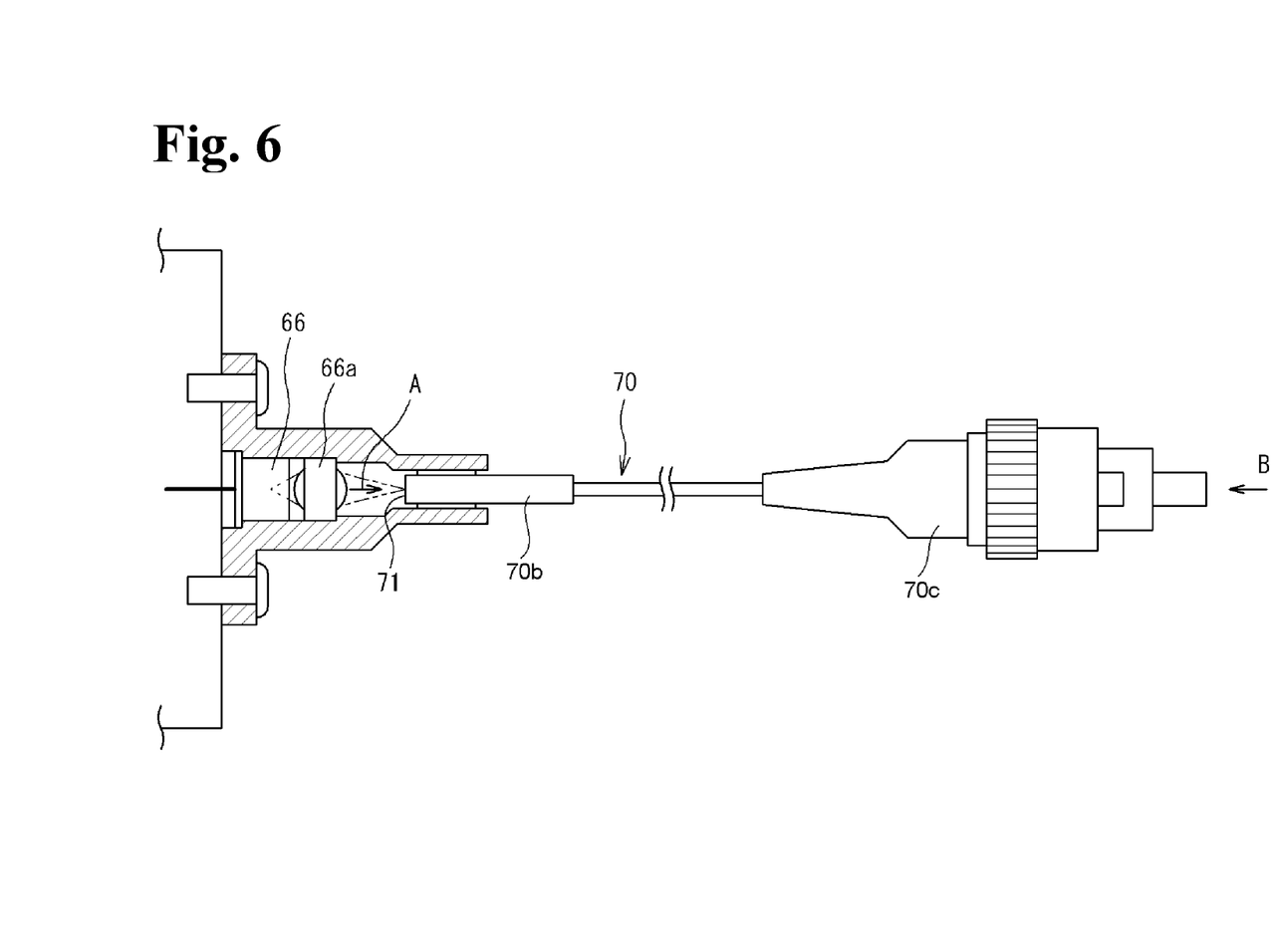
FIG. 6 is a cross sectional view of the optical fiber bundle.
Figure 7A:
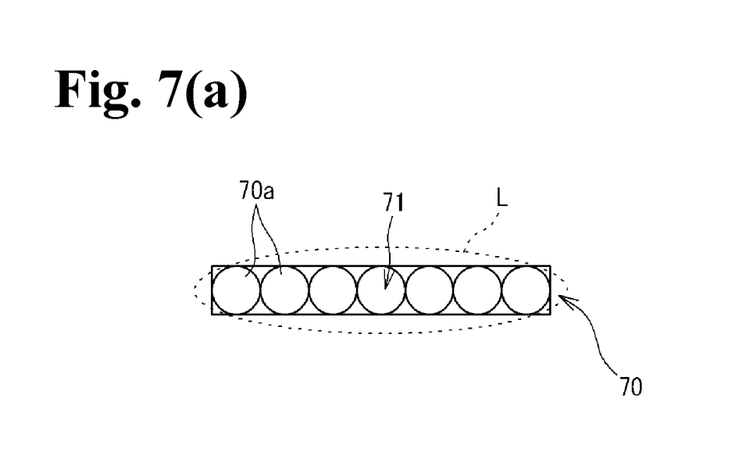

The lens system 60 and optical fiber bundle 70 in the imaging section 26 are described in detail below. FIG. 4 is a side view of the lens system 60; FIG. 5 is a top view of the lens system 60; FIG. 6 is a cross sectional view of the optical fiber bundle 70; FIG. 7(a) is a view on the A arrow of FIG. 6 and FIG. 7(b) is a view on the B arrow of FIG. 6.

As shown in FIG. 5, the optical fiber bundle 70 configured by a bundled plurality of optical fibers is connected to the light source 66. In the present embodiment, a single optical fiber bundle 70 is configured by bundling seven optical fibers 70a, as shown in FIG. 7. The pulse laser light emitted from the light source 66 passes through a condenser lens 66a and enters one end of the optical fiber bundle 70, and is emitted from the other end of the optical fiber bundle 70, as shown in FIG. 6. Note that a filter 70b is provided on the entrance end of the optical fiber bundle 70, and a filter 70c is provided on the exit end of the optical fiber bundle 70.

As shown in FIG. 7(a), the pulse laser light emitted from the light source 66 is long and narrow in the horizontal direction (direction perpendicular to the sample stream direction in the flow cell 51), and the pulse laser light that has passed through the condenser lens 66a is similarly adjusted to a predetermined numerical aperture with a long and narrow shape in the horizontal direction as indicated by the dotted line L. Conversely, the incidence plane 71 of the optical fiber bundle 70 is also long and narrow in the horizontal direction; specifically, the plurality of optical fibers 70a are arranged in a row in the horizontal direction. Thus, the pulse laser light is efficiently introduced into the optical fiber bundle 70 and the amount of light required for imaging particles is readily ensured by forming the incidence plane of the optical fiber bundle 70 in a shape corresponding to the incidence shape of the pulse laser light.

Figure 7B:
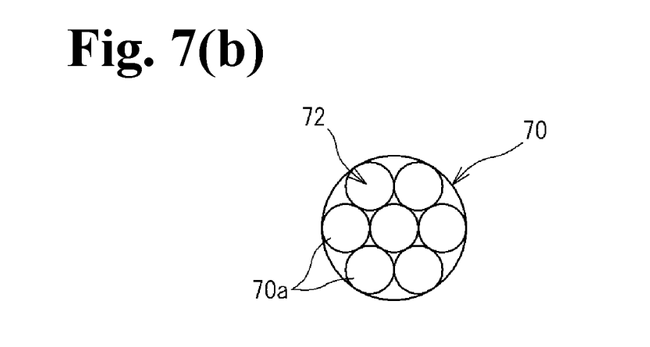

As shown in FIG. 7(b), the emission plane 72 of the optical fiber bundle 70 is circular or a regular hexagonal shape obtained by bundling the plurality of optical fibers 70a so as to have virtually no directionality on the circumferential direction. Therefore, when the emission plane 72 of the optical fiber bundle 70 is disposed toward the lens system 60, there is no need to consider the directionality of the circumferential direction of the emission plane 72 so that the emission plane 72 can be positioned easily.

The optical fiber bundle 70 of the present embodiment has a NA (numerical aperture) of 0.2, core diameter of 114 μm, cladding diameter of 125 μm, SI type multi mode optical fiber 150 mm in length bundled into a fiber bundle. The SI type multi mode optical fiber prevents the generation of interference in the captured image because optical path difference is sufficiently longer than the coherence length (approximately 150 μm) of the pulse laser light from the light source 66. Note that the number and length of the optical fibers 70a in the optical fiber bundle 70 is not limited in the present embodiment, and, for example, a bundle of ten optical fibers 70a having a length of about 100 mm may be used.

As shown in FIGS. 4 and 5, the lens system 60 of the present embodiment is configured by a lens group including a biconvex single lens 60a, plano-convex cylindrical lens 60b, dual R cylindrical lens 60c, dual R spherical lens 60d, and dual R spherical surface cylindrical lens 60e.

As shown in FIG. 5, when the pulse laser light emitted from the optical fiber bundle 70 is viewed from above, the pulse laser light exits and diffuses from the optical fiber bundle 70, enters the biconvex single lens (collimator lens) 60a which changes the rays to parallel light, and the light then passes through the plano-convex cylindrical lens 60b without refraction, and the light is then focused (image formation) at focal point P behind the flow cell 51 by the dual R cylindrical lens 60c, dual R spherical surface lens 60d, and dual R spherical surface cylindrical lens 60e.

As shown in FIG. 4, when the pulse laser light emitted from the optical fiber bundle 70 is viewed from the side, the pulse laser light exits and diffuses from the optical fiber bundle 70, enters the biconvex single lens 60a which converts the rays to parallel light that is diffused by the plano-convex cylindrical lens 60b after having converged in the flow direction F of the measurement sample, then passes through the dual R cylindrical lens 60c without refraction, and is then focused (image formation) at focal point P behind the flow cell 51 by the dual R spherical surface lens 60d and dual R spherical surface cylindrical lens 60e. The camera 65 then images the cells of the sample stream in the flow cell 51 irradiated by the pulse laser light.

In the cell analyzer of the present embodiment described above, an optical fiber bundle 70 configured by a plurality of optical fibers 70a is used as the optical path between the light source 66 and the flow cell 51. Conventionally, the speckle noise generated in images is caused by random interference between modes within the optical fiber, distortion of the core diameter and defects within the optical fiber 70a, and expansion of the core diameter due to temperature fluctuation when a single optical fiber is used; however, in the present embodiment, the speckle noise overlaps and is smoothed by bundling a plurality of optical fibers 70a even though the individual optical fibers 70a produced speckle noise. Therefore, the speckle noise can be reduced overall, and the camera 65 can obtain sharp particle images containing very little noise.

Figure 8:
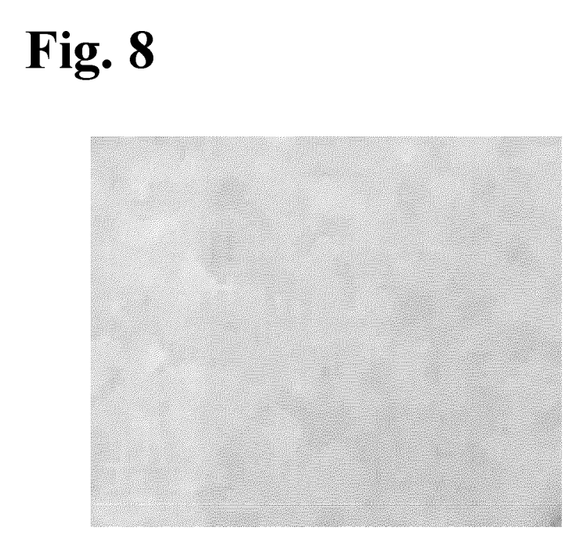
FIG. 8 is a background image captured by the imaging section of the present embodiment.

FIG. 8 is a background image captured by the imaging section of the present embodiment using an optical fiber bundle, and FIG. 9 is a background image captured by a conventional imaging section using a single optical fiber. As shown in FIG. 9, the entire background has a black and white spotted pattern, that is, speckle noise, whereas the present embodiment reduces speckle noise and has very little black and white dotted pattern, as shown in FIG. 8.

The pulse laser light can suppress the interference fringes because coherency is reduced when the pulse laser light passes through the optical fibers 70a. Note that the NA of the lens system 60 that irradiates the pulse laser light on the flow cell 51 is preferably set at 0.1 or higher, for example, 0.155, to sufficiently reduce visible interference fringe of particles of approximately φ5 μm in diameter.

Since the imaging section 26 of the present embodiment uses the optical fiber bundle 70 configured by a plurality of optical fibers 70a, the pulse laser light emitted from each optical fiber 70a and that has passed through the lens system 60 arrives at the focal point position P and the difference in brightness of each optical fiber 70a and gap between each optical fiber a is also transferred directly. Therefore, a problem of irregular illumination occurs when the pulse laser light irradiates the sample stream at the focal position P. In the present embodiment, this problem if irregular illumination caused by the pulse laser light irradiating the sample stream is prevented by shifting the focal point P so that the pulse laser light that has passed through the lens system 60 arrives at the focal point P disposed behind the sample stream (defocusing).

Note that the focal point position P of the pulse laser light emitted from the individual optical fibers 70a also may be positioned anterior to the sample stream, so that the irregular illumination is prevented thereby for a similar reason. The distance L (refer to FIG. 5) between the sample stream and the focal point position P is set at 1.0 to 2.0 mm (for example, 1.6 mm); the spot size of the illuminated part of the sample stream is also set at a size sufficiently larger than the diameter of the cells, for example, approximately 2 mm.

The image data obtained by the imaging section 26 is transmitted by the microprocessor 20 of the measurement controller 16 to the system controller 13 through the external communication controller 25, whereupon the data are stored on the hard disk, and thereafter the data and the analysis results are displayed together on the display section 28 (refer to FIG. 1).

Figure 10:
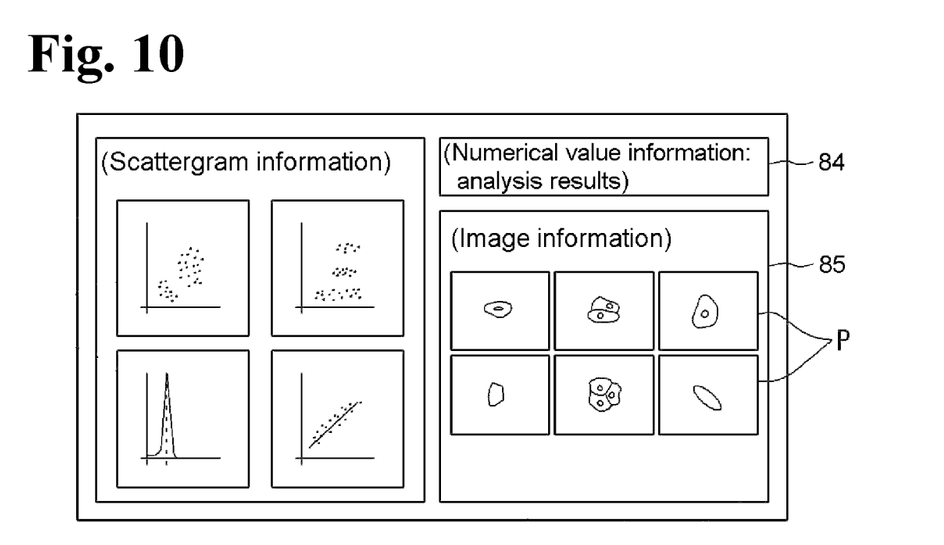
FIG. 10 shows a brief example of the screen structure of the display section.

FIG. 10 shows a brief example of the screen structure of the display section 28. As shown in FIG. 10, the screen of the display section 28 has an analysis result display part 84 for displaying analysis results such as scattergrams, number of abnormal cells, and abnormal cell ratio, and an image display part 85 for displaying the image P of the abnormal cell imaged by the imaging section 26. The image display part 85 can simultaneously display a plurality (six in the example of the drawing) of images P; the cell pathologist can comprehend the morphology of the abnormal cell by directly viewing the image P. Since the particle image obtained by the imaging section 26 is a clear image without interference fringe or speckle noise, the user can visually confirm the morphology of the cell and properly determine whether the cell is an abnormal cell. The determination also may be reflected in the analysis result such as the abnormal cell ratio.

Note that the embodiments of the present disclosure are in all respects examples and are not to be considered as limiting in any way. The scope of the present invention is defined solely by the appended claims, is not affected to any degree by the statements within this summary, and includes all modifications which fall within the meanings and equivalences of the scope of the claims.

For example, the specifications may be modified, such as the number of optical fibers 70a that configure the optical fiber bundle 70, the core diameter, length and NA of the optical fibers 70a and the like; and the configuration of the lenses that configure the lens group 60 also may be suitably modified.

The cell analyzer of the above embodiment is not limited to analyzing cervical epithelial cells inasmuch as the cell analyzer also may be used to analyze various other cells (particles) such as buccal cells, epithelial cells of the bladder and throat, and blood cells.

In the above embodiment, a pulse laser light source that emits pulse light is used as the light source 66. However, the present invention is not limited to this light source. For example, a laser light source that emits continuous light also may be used as the light source 66.

What is claimed is:

1. An analyzer, comprising:
a sample stream forming section for forming a sample stream including cells;
a first light source;
an optical fiber bundle formed by a plurality of multi-mode optical fibers, into which light from the light source enters;
a lens system for collecting the light emitted from the optical fiber bundle onto the sample stream;
an imaging device for imaging a cell in the irradiated sample stream;
a second light source for irradiating the sample stream with light;
a light receiving section for receiving light generated from the sample stream irradiated by the second light source; and
a controller configured to:
obtain a parameter of a cell based on the light received by the light receiving section;
determine whether the parameter satisfies a condition for detecting an abnormal cell; and
control the imaging device to image the cell when the parameter of the cell satisfies the condition.

2. The analyzer of claim 1, wherein
an incidence plane of the optical fiber bundle into which the light from the light source enters is formed with a shape corresponding to a shape of the light emitted from the first light source.

3. The analyzer of claim 2, wherein
the shape of the light emitted from the first light source is elongated; and
the plurality of optical fibers configuring the optical fiber bundle are arranged lengthwise to match the elongated light emitted from the first light source.

4. The analyzer of claim 2, wherein
the shape of the incidence plane of the optical fiber bundle is different from a shape of an emission plane of the optical fiber bundle from which the light emits.

5. The analyzer of claim 1, wherein
the emission plane of the optical fiber bundle has a substantially circular shape or regular polygonal shape.

6. The analyzer of claim 1, wherein
the cells are epithelial cells collected from a cervix.

7. The analyzer of claim 1, wherein
the sample stream forming section comprises a flow cell for forming the sample stream by surrounding a sample containing the cells with a sheath liquid.

8. The analyzer of claim 1, wherein
the first light source emits pulse laser light.

9. The analyzer of claim 1, comprising
a display for displaying the determination result of the determining section and a cell image obtained by the imaging device.

10. A cell imaging method, comprising steps of:
forming a sample stream including cells;
guiding light from a light source into an optical fiber bundle formed by a plurality of multi-mode optical fibers;
collecting the light emitted from the optical fiber bundle onto the sample stream;
determining whether a cells is an abnormal cell based on light generated from the sample stream when the sample stream is irradiated by light;
imaging the cells in the irradiated sample stream;
Wherein in the imaging step, a cell is imaged when the cell is the abnormal cell.

11. The cell imaging method of claim 10, wherein
an incidence plane of the optical fiber bundle into which the light from the light source enters is formed with a shape corresponding to a shape of the light emitted from the light source.

12. The cell imaging method of claim 11, wherein
the shape of the light emitted from the light source is elongated; and
the plurality of optical fibers configuring the optical fiber bundle are arranged lengthwise to match the elongated light emitted from the light source.

13. The cell imaging method of claim 10, wherein
the emission plane of the optical fiber bundle has a substantially circular shape or regular polygonal shape.

14. The cell imaging method of claim 10, wherein
in the step of emitting light on the sample stream, the light emitted from the optical fiber bundle is concentrated at a position anterior to the sample stream or a position beyond the sample stream.

15. The cell imaging method of claim 10, wherein
the cells are epithelial cells collected from a cervix.

16. The cell imaging method of claim 10, comprising steps of:
displaying an image of a cell together with a result of the determination of whether the cell is the abnormal cell.

17. The cell imaging method of claim 10, wherein the optical fiber bundle is provided in a bent state.

18. The analyzer of claim 1, Wherein
nuclei of the cells are stained, and
the determining section determines based on fluorescent light signal received by the light receiving section.

19. The analyzer of claim 1, wherein the optical fiber bundle is provided between the first light source and the lens system in a bent state.

20. The analyzer of claim 1, further comprising
a display,
wherein the display is configured to display at least one of:
a scattergram having axes of signal waveform pulse width of scattered light and signal waveform peak value of scattered light; and
a scattergram having axes of value of obtained by dividing the integral difference of the fluorescent light signal waveform by peak value of the fluorescent light signal waveform and signal waveform pulse width of scattered light.

* * * * *